US011173032B2

(12) United States Patent
Zeng (10) Patent No.: US 11,173,032 B2
(45) Date of Patent: Nov. 16, 2021

(54) TRANSCATHETER DEVICE FOR TREATING MITRAL REGURGITATION (71) Applicant: Edwards Lifesciences Corporation, Irvine, CA (US)

(72) Inventor: Qinggang Zeng, Mission Viejo, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 57 days.

(21) Appl. No.: 16/112,388

(22) Filed: Aug. 24, 2018

(65) Prior Publication Data

US 2019/0060072 A1 Feb. 28, 2019

Related U.S. Application Data (60) Provisional application No. 62/550,798, filed on Aug. 28, 2017.

(51) Int. Cl.
*A61F 2/24* (2006.01)
(52) U.S. Cl.
CPC ............ *A61F 2/2463* (2013.01); *A61F 2/246* (2013.01); *A61F 2/2445* (2013.01); *A61F 2/2427* (2013.01); *A61F 2/2457* (2013.01); *A61F 2/2466* (2013.01); *A61F 2210/0014* (2013.01); *A61F 2220/0008* (2013.01)
(58) Field of Classification Search
CPC ......... A61F 2/2442–2/2463; A61F 2210/0014; A61F 2220/0008; A61F 2230/0008; A61F 2230/0067; A61F 2250/0039; A61F 2250/0069; A61F 2/2427; A61F 2/2466
See application file for complete search history.

(56) References Cited

U.S. PATENT DOCUMENTS

| 8,968,395 | B2 | 3/2015 | Hauser et al. | |
| 10,786,351 | B2* | 9/2020 | Christianson | ......... A61F 2/2439 |
| 10,980,632 | B2* | 4/2021 | Burriesci | ............. A61F 2/2436 |
| 10,993,806 | B2* | 5/2021 | Thambar | ............... A61F 2/2436 |
| 2005/0010287 | A1* | 1/2005 | Macoviak | ............. A61F 2/2454 623/2.36 |
| 2009/0043382 | A1 | 2/2009 | Maurer et al. | |
| 2011/0066233 | A1 | 3/2011 | Thornton et al. | |
| 2012/0059458 | A1* | 3/2012 | Buchbinder | .......... A61F 2/2409 623/2.36 |
| 2014/0012368 | A1* | 1/2014 | Sugimoto | ............... A61F 2/915 623/2.11 |

(Continued)

FOREIGN PATENT DOCUMENTS

| EP | 3184081 A1 | 6/2017 | |
| WO | 2015061533 A1 | 4/2015 | |
| WO | WO-2019046241 A1 * | 3/2019 | ........... A61F 2/2463 |

*Primary Examiner* — Paul B Prebilic
(74) *Attorney, Agent, or Firm* — Alan T. Hale; Chang & Hale LLP (57) ABSTRACT The invention is a prosthetic device for improving function of a mitral valve. The device includes a sealing member configured for positioning between mitral valve leaflets. The device also includes an expandable anchor frame configured to be positioned within one or more heart chambers, for maintaining the sealing member at a desired position between valve leaflets. The sealing member reduces mitral regurgitation be filling the gap that can occur between opposing leaflets of a damaged mitral valve, thus restoring proper mitral valve closure.

15 Claims, 8 Drawing Sheets

(56) References Cited

U.S. PATENT DOCUMENTS

| | | |
|---|---|---|
| 2014/0012372 A1 | 1/2014 | Chau et al. |
| 2014/0067054 A1 | 3/2014 | Chau et al. |
| 2014/0324164 A1* | 10/2014 | Gross .................... A61F 2/2436 623/2.37 |
| 2015/0025623 A1* | 1/2015 | Granada ............... A61F 2/2412 623/2.11 |
| 2015/0173898 A1 | 6/2015 | Drasler et al. |
| 2016/0166382 A1 | 6/2016 | Nguyen |
| 2016/0199181 A1 | 7/2016 | Kramer |

\* cited by examiner

TRANSCATHETER DEVICE FOR TREATING MITRAL REGURGITATION

CROSS-REFERENCE TO RELATED APPLICATIONS

This application claims the benefit of U.S. Provisional Patent Application No. 62/550,798, filed Aug. 28, 2017.

FIELD OF THE INVENTION

The present invention relates to the repair of heart valves, and, more particularly, to methods and apparatuses for the repair of heart valves by positioning a device between valve leaflets to improve valve closure.

BACKGROUND OF THE INVENTION

In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves separate the chambers of the heart, and are each mounted in an annulus therebetween. The annuluses comprise dense fibrous rings attached either directly or indirectly to the atrial and ventricular muscle fibers. The leaflets are flexible collagenous structures that are attached to and extend inward from the annuluses to meet at coapting edges. The aortic, tricuspid, and pulmonary valves usually have three leaflets, while the mitral valve usually has two leaflets.

The operation of the heart, and thus the patient's health, may be seriously impaired if any of the heart valves is not functioning properly. Various problems can develop with heart valves for a number of clinical reasons. Stenosis in heart valves is a condition in which the valves do not open properly. Insufficiency is a condition which a valve does not close properly. Repair or replacement of the aortic or mitral valves are most common because they reside in the left side of the heart where pressures and stresses are the greatest. In a valve replacement operation, a replacement prosthetic valve is implanted into the native valve annulus, which may involve excision of the native valve leaflets.

In many patients who suffer from valve dysfunction, surgical or percutaneous repair (i.e., "valvuloplasty") is a desirable alternative to valve replacement. Remodeling of the valve annulus (i.e., "annuloplasty") is central to many reconstructive valvuloplasty procedures. Remodeling of the valve annulus is typically accomplished by implantation of a prosthetic ring (i.e. "annuloplasty ring") to stabilize the annulus and to correct or prevent valvular insufficiency that may result from a dysfunction of the valve annulus. Annuloplasty rings are typically constructed of a resilient core covered with a fabric sewing ring. Annuloplasty procedures are performed not only to repair damaged or diseased annuli, but may also be performed in conjunction with other procedures, such as leaflet repair.

Heart valves may lose their ability to close properly due to dilation of an annulus around the valve or a flaccid, prolapsed leaflet. The leaflets may also have shrunk due to disease, such as rheumatic disease, thereby leaving a gap in the valve between the leaflets. The inability of the heart valve to close will cause blood to leak backwards (opposite to the normal flow of blood), commonly referred to as regurgitation. Common examples of such regurgitation include mitral valve regurgitation (i.e., leakage of blood through the mitral valve and back into the left atrium) and aortic valve regurgitation (i.e., leakage through the aortic valve back into the left ventricle). Regurgitation may seriously impair the function of the heart since more blood will have to be pumped through the regurgitating valve to maintain adequate circulation.

Heart valve regurgitation decreases the efficiency of the heart, reduces blood circulation, and adds stress to the heart. In early stages, heart valve regurgitation leaves a person fatigued and short of breath. If left unchecked, the problem can lead to congestive heart failure, arrhythmias, or death.

Mitral valve regurgitation may be caused by dysfunction of the mitral valve structure, such as may result from direct injury to the mitral valve leaflets. Such regurgitation can be caused by changes in the shape of the mitral valve annulus, damage to the posterior and/or anterior leaflets, and/or damage to the chordae tendinae. In such regurgitation, the anterior and posterior leaflets no longer coapt together properly to seal the valve, so that instead of the anterior and posterior leaflets coapting to fully close the mitral valve annulus during systole, an opening remains between the edges of the anterior and posterior leaflets.

Various methods of mitral valve repair are known in the art. Implantation of an annuloplasty ring, typically around the posterior aspect of the mitral valve, has proven successful in a number of cases. Such annuloplasty rings reshape the surrounding annulus, which can lead to proper coaptation of the native leaflets. Another repair technique for the mitral valve is known as a "bow-tie" repair, which involves suturing the anterior and posterior leaflets together in edge-to-edge fashion toward the middle of the leaflets, causing blood to flow through the two side openings thus formed. This process was originally developed by Dr. Ottavio Alfieri, and involved placing the patient on extracorporeal bypass in order to access and suture the mitral valve leaflets. Later adaptations of the bow-tie technique involved beating-heart repairs using percutaneous methods, such using a catheter to install suture or a clip to secure the opposing leaflets together.

Another approach to repairing a native valve having non-coapting leaflets, including mitral and aortic valves, involves inserting a device between the leaflets, with the device being sized and positioned to block the gap between the otherwise non-coapting leaflets. Examples of such repair devices and techniques are disclosed in U.S. Pat. No. 8,968,395 to Hauser et al. and U.S. Patent Pub. No. 2009/0043382 for Maurer et al. These disclose devices which include an anchor deployed in the lower ventricle which secures a blocking device within the mitral valve annulus.

There is presently a need for an improved means for performing heart valve repair. The current invention fulfills this need.

SUMMARY OF THE INVENTION

The present invention provides a number of devices and methods for improving valve function. The devices and methods herein reduce or eliminate valve regurgitation without interfering with normal valve function, i.e., not impeding the natural motion of the leaflets, chordae tendinae, or papillary muscles.

It should be understood that each of the sealing elements disclosed herein can be used with any and all of the anchor elements disclosed herein, even though the specific combination of sealing element with anchor elements may not be explicitly shown in the figures herein. In other words, based on the explanation of the particular device, one of skill in the art should have little trouble combining the features of certain of two such devices. Therefore, it should be understood that many of the sealing and anchor elements are interchangeable, and the invention covers all permutations thereof. Moreover, each of the sealing elements may be used alone or in combination with other anchor devices. Each of the anchor elements can be used alone or in combination with other implant devices.

The devices of the present invention can be utilized in standard open surgical procedures, minimally-invasive procedures, or percutaneous procedures. In one embodiment the devices can be delivered through an open chest, e.g., transapically or transatrially. In another embodiment, the devices can be introduced through an incision performed over the roof of the left atrium. In yet another embodiment the devices can be delivered into the left ventricle through the right chest via a thoracscope, which may be performed transapically. The devices can also be delivered percutaneously, such as via a catheter or catheters into the patient's arterial system (e.g. through the femoral or brachial arteries).

Advantages of the device include a low delivery profile, which is conducive to minimally-invasive and percutaneous delivery methods. The device is configured to interact properly with the native leaflets, ventricle, atrial, and subvalvular apparatus. The device preserves rather than obstructs the mobility and dynamic motion of the native leaflets (except as necessary for proper coaptation). The native leaflets and chordae tendinae are preserved, and continue to operate (including opposing the systolic closing pressure). The subvalvular process and left ventricle coordination are thus preserved. The device may be configured so that it does not expand the native mitral valve leaflets or annulus outward, so that left ventricular outflow tract (LVOT) impingement/obstruction should not be a concern. The shape and low profile of the sealing element minimizes flow resistance during diastole, and there are no areas of stasis created by the device. A single device can be applicable to a wide range of valve sizes.

The device may be applicable to numerous mitral valve regurgitation conditions, including those caused by leaflet prolapse with varying amounts of annular dilatation (type I), focal leaflet prolapse (type II), and leaflet tethering (type IIIb).

Embodiments of the present disclosure provide devices and methods for improving the function of a defective heart valve, such as a mitral valve. The devices and methods disclosed herein are desirably delivered into a subject's heart using percutaneous or minimally invasive surgical methods. Accordingly, desirable delivery methods described herein do not require extracorporeal circulation (e.g., blood from a subject's circulation being routed outside the body to have a process applied to and then, returned of the subject's circulation). For example, in one embodiment, a delivery catheter (or similar delivery device) is inserted through an incision in the chest wall and then through the cardiac tissue (e.g., through the apex of the heart) into a chamber of the patient's beating heart. The delivery catheter can allow a prosthetic device to be delivered into the heart in a collapsed configuration and then expanded within the heart for treating a defective heart valve. Because the desired delivery methods do not require extracorporeal circulation, complications are greatly reduced as compared with traditional open-heart surgery.

An embodiment of the invention for treating a mitral valve is a device that includes a prosthetic sealing member having an elongated cross-sectional profile, the sealing member shaped for contacting the leaflets of the mitral valve. The device also includes an anchoring member coupled to the sealing member and configured to secure the sealing member at a desired position between the mitral valve leaflets. The sealing member and anchoring member may be radially collapsible and radially expandable, which may permit the device to be delivered and deployed via a catheter.

The anchoring member may have an upper portion configured to extend around a mitral valve annulus and contact atrial tissue adjacent the mitral valve annulus, a lower portion configured to extend around native valve leaflets and engage ventricular tissue adjacent the mitral valve annulus without interfering with the movement of the mitral valve leaflets, and a central portion configured to support the sealing member. The anchor element upper portion may have a continuous loop defining a circumference approximating a mitral valve annulus of a human. The upper portion may have a plurality of radially-extending arms to engage heart tissue such as atrial tissue adjacent a mitral valve. The lower portion may have a plurality of radially-extending arms to engage heart tissue such as ventricular tissue adjacent a mitral valve, and may be dimensioned such when the lower portion is deployed the native valve leaflets can open and close as the heart beats with limited or no interference from the lower portion. In one embodiment of the device, the native valve leaflets are unrestricted in their opening and closing by any and all portions of the device except for the sealing element, which engages the native valve leaflets during systole to form a seal between the native leaflets and thereby prevent mitral valve regurgitation.

An anchoring member according to the invention may be configured so that the anchoring member does not expand the native mitral valve annulus, because such annulus expansion might otherwise cause reduction in valve efficiency. For example, the anchoring member may be configured so it does not subject the native mitral valve annulus to radially-expansive forces. The anchoring member may be configured so that the lower anchor portion presses upward against the native valve annulus while the upper anchor portion presses downward against the native valve annulus, so that tissue of the native valve annulus is held between the lower anchor portion and the upper anchor portion but the annulus is not subjected to radially-expansive forces from the anchoring member. Such embodiments may even prevent further annulus expansion by securing the annulus between the opposing anchor portions.

An anchoring member according to the invention may be self-expandable, such as via construction of a memory material such as nitinol. The anchoring member may alternatively be formed of other materials, such as stainless steel or cobalt chromium.

The anchor element may have a plurality of radially-extendable arms for engaging heart tissue. The anchor element lower portion may have an anterior arm extending in a first direction, the anterior arm curving up from a bottom of the anchor element toward a top of the anchor element in order to permit the anterior leaflet to swing unhindered by the anterior arm. the anchor element may have a posterior arm extending in a second direction, wherein the second direction is opposite to the first direction, with the posterior arm curving up from a bottom of the anchor element toward a top of the anchor element outside of the swing area of a posterior leaflet to permit the posterior leaflet to swing without engaging the posterior arm. The anchor element lower portion may have an anterior finger extending sideways away from the anterior arm at an anterior arm distal end, and may have a posterior finger extending sideways from the posterior arm at a distal end thereof.

The sealing element is dimensioned to be deployed in an annulus of a native mitral valve of a heart at a position between native mitral valve leaflets to contact the native mitral valve leaflets during ventricular systole to create a seal to prevent regurgitation of blood from the left ventricle to the left atrium, while permitting the native mitral valve leaflets to open and close as the heart beats. The sealing element may have an upper end, a lower end, an anterior surface, and a posterior surface. The anterior surface may be configured to coapt with a mitral valve anterior leaflet, and the posterior surface may configured to coapt with a mitral valve posterior leaflet. The sealing element may be wider toward a top portion thereof and taper to a lower portion thereof.

The sealing element may preferably wrap around the exterior and/or interior of the central anchor portion, so that the wireform elements of the central anchor portion are covered and/or encapsulated by the sealing element in order to prevent the native valve leaflets from contacting any frame elements of the central anchor portion.

The sealing element may have a proximal opening and a distal opening with passageway between the proximal and distal openings for allowing blood to flow through the sealing member from the left atrium to the left ventricle, and the proximal opening may be larger than the distal opening. The sealing element may have an outer layer defining an outer surface of the sealing member, with the outer layer comprising a biological material to inhibit abrasion of the leaflets of the mitral valve when the leaflets contact the outer surface of the sealing member.

A system for treating a mitral valve according to an embodiment of the invention may have a delivery catheter, an anchor member, and a prosthetic sealing member. The anchor member may have an upper portion, a lower portion, and a central portion. The anchoring member may be self-expanding, and may have a plurality of radially-extendable arms for engaging heart tissue. The sealing member may be adapted for plugging a gap between the leaflets of the mitral valve and reducing regurgitation. The prosthetic sealing member may have a collapsed state and an expanded state, with the sealing member has an elongated cross-sectional profile in the expanded state for insertion between the leaflets of the mitral valve. The sealing member may have an outer surface formed with biological tissue. The elongated cross-sectional profile of the sealing member may be solid such that blood is forced to flow around the sealing member.

A method according to the invention for improving the function of a heart valve may involve advancing a distal end of a delivery catheter to a position at a mitral or other heart valve of a patient, wherein within the distal end is a prosthetic device having an anchor member and a sealing member. The sealing member may be configured to expand into a configuration to reduce regurgitation through the mitral valve. The anchor member may have an upper portion configured to expand into engagement with atrial tissue, a central portion configured to expand to support the sealing member, and a lower portion configured to expand into engagement with ventricular tissue. The anchor member may have a self-expandable frame that is mounted in a compressed state within a distal end of the delivery catheter. The method may further include releasing the anchor member upper portion from the catheter at a position such that the anchor member upper portion engages atrial tissue adjacent an annulus of the mitral valve; releasing the anchor member central portion and the sealing member from the catheter; and then releasing the anchor member lower portion from the catheter at a position such that the anchor member lower portion engages ventricular tissue adjacent an annulus of the mitral valve. This deployment procedure could also be reversed, i.e., releasing the anchor member lower portion first, then the central portion/sealing member, and then the upper portion. After deployment of the anchor member portions and the sealing member, the sealing member should be positioned between leaflets of the mitral valve such that during systole the leaflets coapt against the sealing member. The device may be delivered and deployed using various delivery techniques, such as percutaneously or transapically to the mitral or other heart valve.

Other objects, features, and advantages of the present invention will become apparent from a consideration of the following detailed description.

DETAILED DESCRIPTION OF SEVERAL EMBODIMENTS

Figure 1:
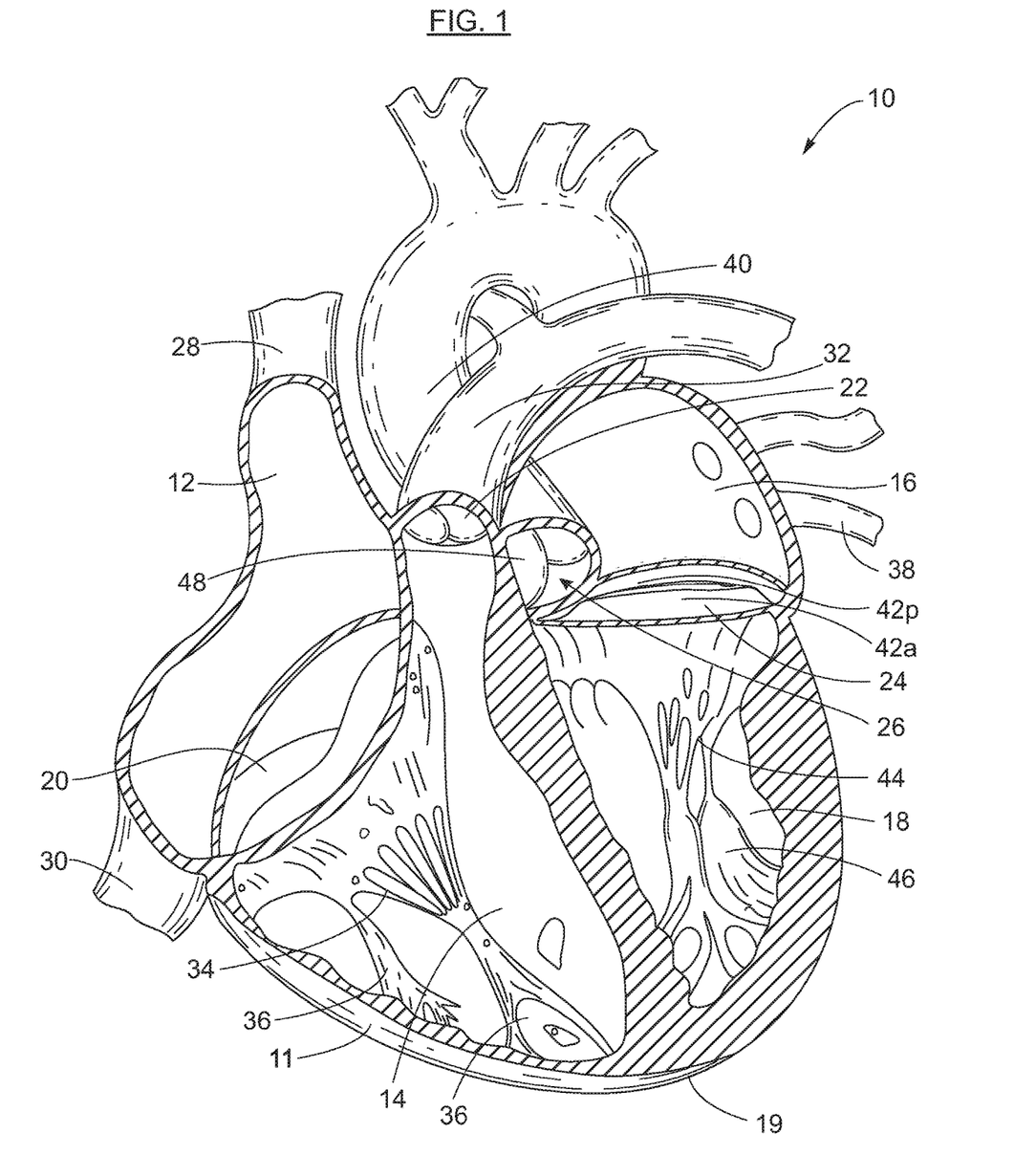
FIG. 1 is a cross-sectional view of a heart.

A cross-sectional view of a human heart 10 is depicted in FIG. 1. The heart 10 has a muscular heart wall 11, an apex 19, and four chambers: right atrium 12; right ventricle 14; left atrium 16; and left ventricle 18. Blood flow is controlled by four main valves: tricuspid valve 20; pulmonary valve 22; mitral valve 24; and aortic valve 26. Blood flows through the superior vena cava 28 and the inferior vena cava 30 into the right atrium 12 of the heart 10. The right atrium 12 pumps blood through the tricuspid valve 20 (in an open configuration) and into the right ventricle 14. The right ventricle 14 then pumps blood out through the pulmonary valve 22 and into the pulmonary artery 32 (which branches into arteries leading to the lungs), with the tricuspid valve 20 closed to prevent blood from flowing from the right ventricle 14 back into the right atrium. Free edges of leaflets of the tricuspid valve 20 are connected via the right ventricular chordae tendinae 34 to the right ventricular papillary muscles 36 in the right ventricle 14 for controlling the movements of the tricuspid valve 20.

After leaving the lungs, the oxygenated blood flows through the pulmonary veins 38 and enters the left atrium 16 of the heart 10. The mitral valve 24 controls blood flow between the left atrium 16 and the left ventricle 18. The mitral valve 24 is closed during ventricular systole when blood is ejected from the left ventricle 18 into the aorta 40. Thereafter, the mitral valve 24 is opened to refill the left ventricle 18 with blood from the left atrium 16. Free edges of leaflets 42*a*, 42*p* of the mitral valve 24 are connected via the left ventricular chordae tendinae 44 to the left ventricular papillary muscles 46 in the left ventricle 18 for controlling the mitral valve 30. Blood from the left ventricle 18 is pumped through the aortic valve 26 into the aorta 40, which branches into arteries leading to all parts of the body except the lungs. The aortic valve 26 includes three leaflets 48 which open and close to control the flow of blood into the aorta 40 from the left ventricle 18 of the heart as it beats.

Figure 2A:
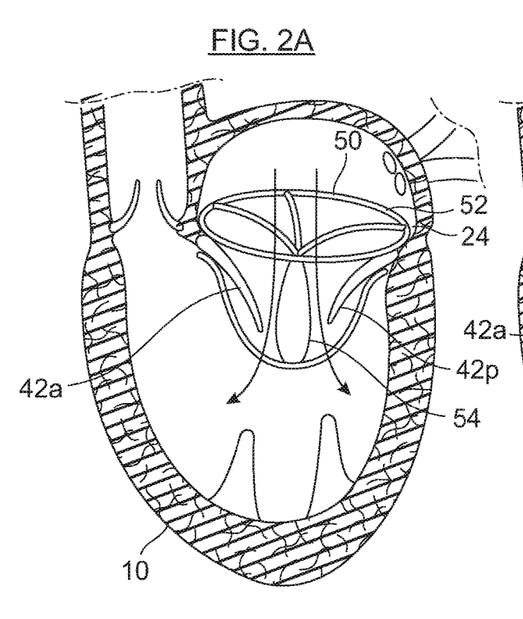
FIGS. 2A-2D depict side cross-sectional views of a heart with a repair device deployed therein according to an embodiment of the invention.
Figure 2B:
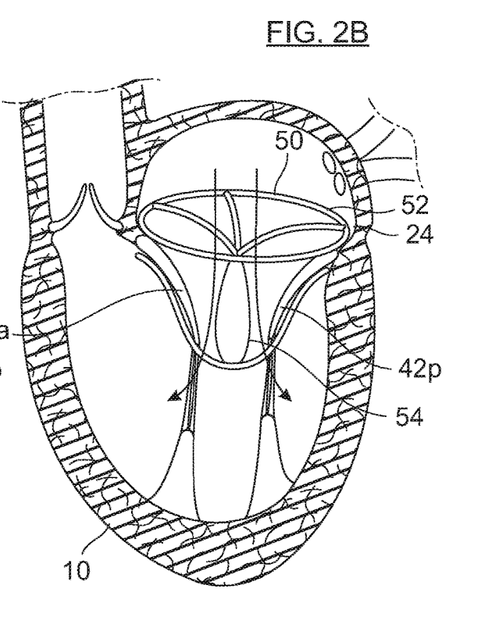
Figures 2C, 2D:
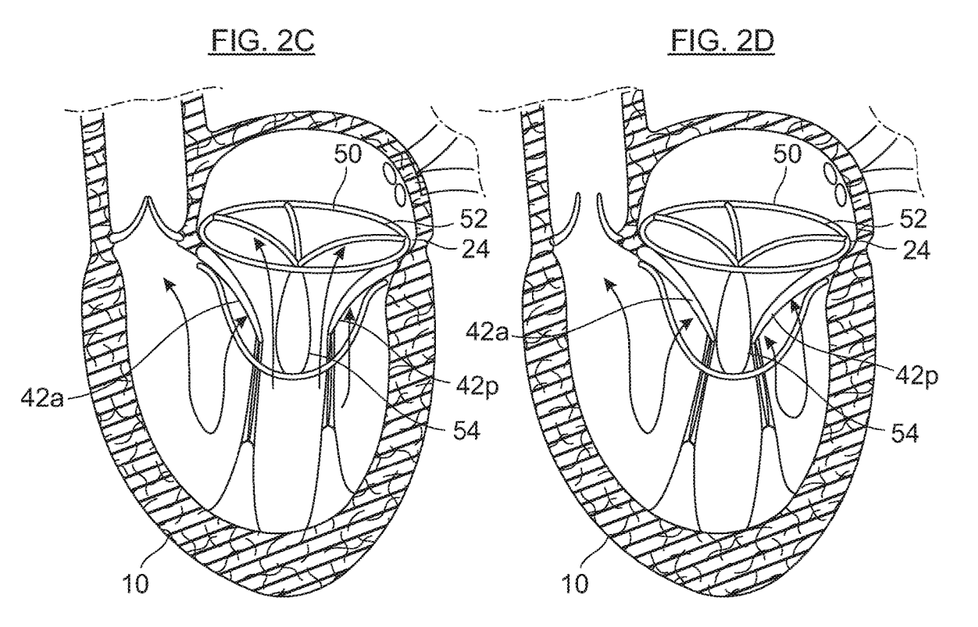

FIGS. 2A-2D depict a device 50 deployed in a native mitral valve 24 according to an embodiment of the invention. The device 50 has a support anchor 52 and a sealing element 54. The support anchor 52 is configured to permit free movement of the native valve leaflets 42*a*, 42*p*. In FIG. 2A, the native mitral valve 24 is in early diastole, with the native leaflets 42*a*, 42*p* starting to open and permit blood to flow from the left atrium 16 to fill the left ventricle 18. In full diastole as depicted in FIG. 2B, the mitral valve leaflets 42*a*, 42*p* are fully open. In early systole as depicted in FIG. 2C, initial backward flow into the left atrium 16 pushes the mitral valve leaflets 42*a*, 42*p* back (upwards) and into engagement with each other and with the sealing element 54. In full systole as depicted in FIG. 2D, the native mitral valve leaflets 42*a*, 42*p* wrap tightly against the sealing element 54 under peak systolic pressure, effectively eliminating any regurgitation flow.

Figure 3A:
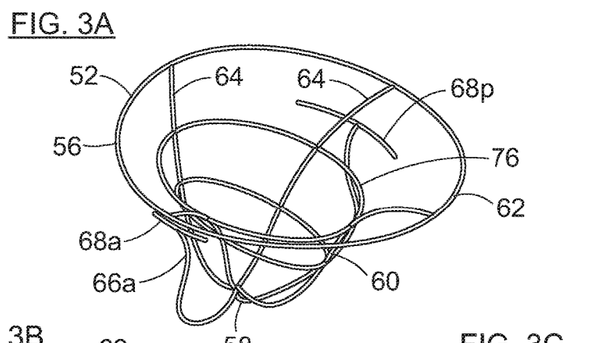
FIGS. 3A-3C depict perspective (posterior), side, and side (anterior) views, respectively, of a support anchor frame element according to an embodiment of the invention.
Figure 3B:
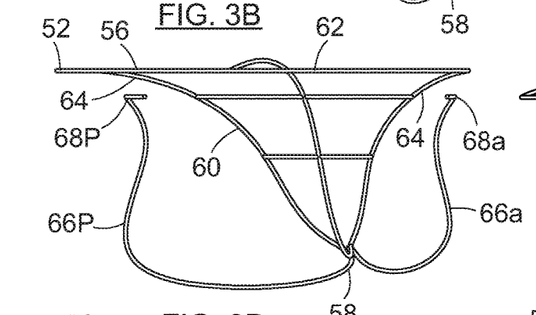
Figure 3C:
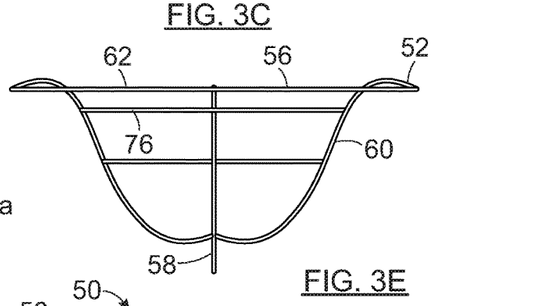
Figure 3D:
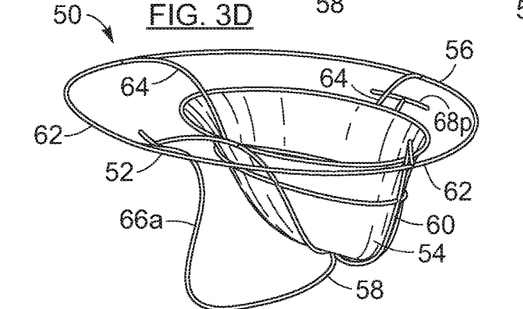
FIGS. 3D-3G depict perspective (anterior), perspective (posterior), side, and top views, respectively, of a repair device according to an embodiment of the invention.
Figure 3E:
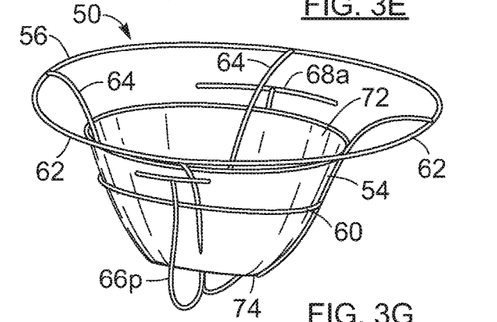
Figure 3F:
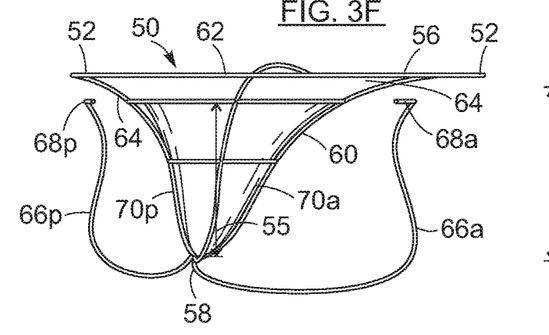
Figure 3G:
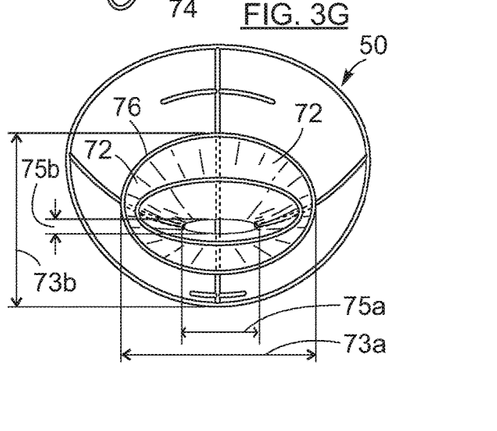
Figure 4A:
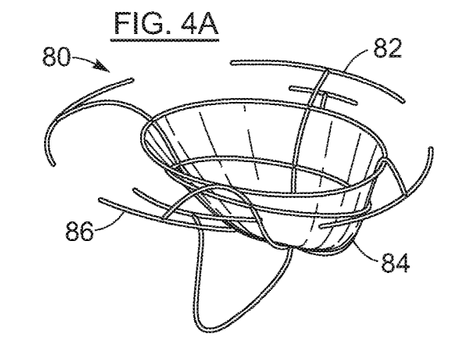
FIGS. 4A-4D depict perspective (anterior), perspective (posterior), side, and top views, respectively, of a repair device according to an embodiment of the invention.
Figure 4B:
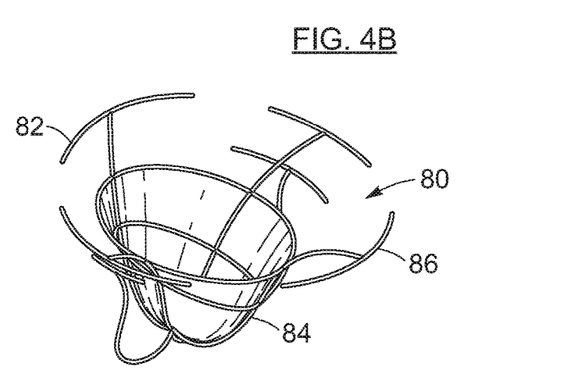
Figure 4C:
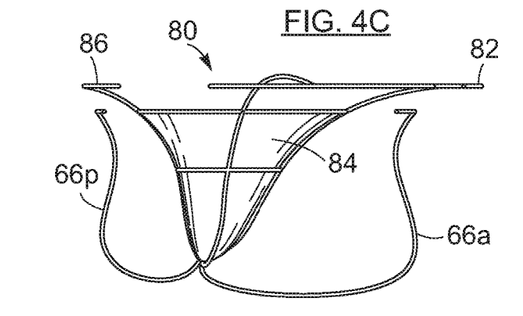
Figure 4D:
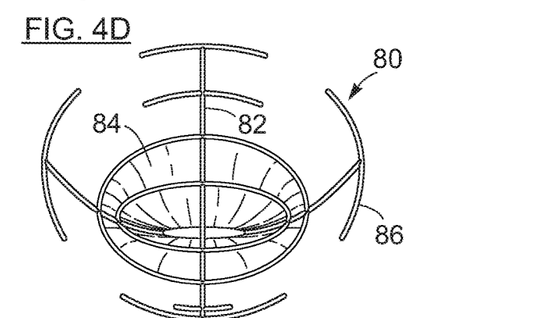
Figure 5A:
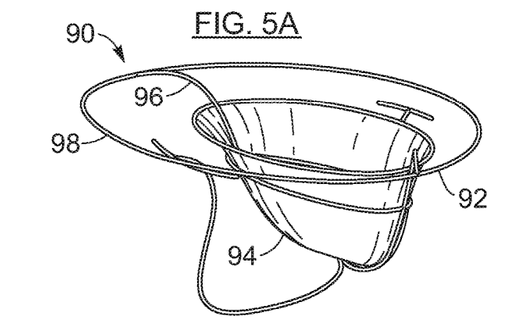
FIGS. 5A-5D depict perspective (anterior), perspective (posterior), side, and top views, respectively, of a repair device according to an embodiment of the invention.
Figure 5B:
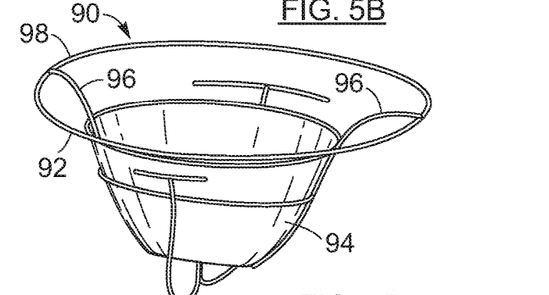
Figure 5C:
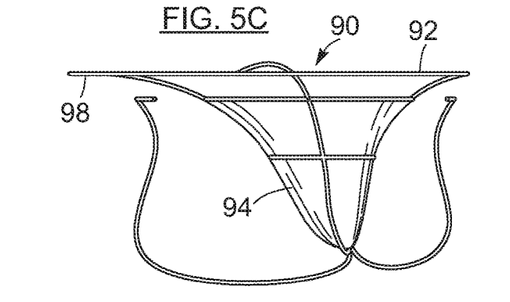
Figure 5D:
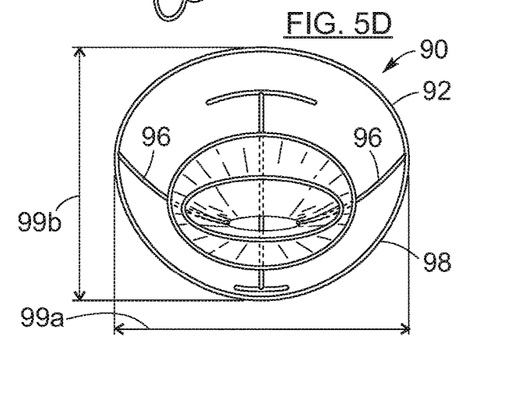
Figure 6A:
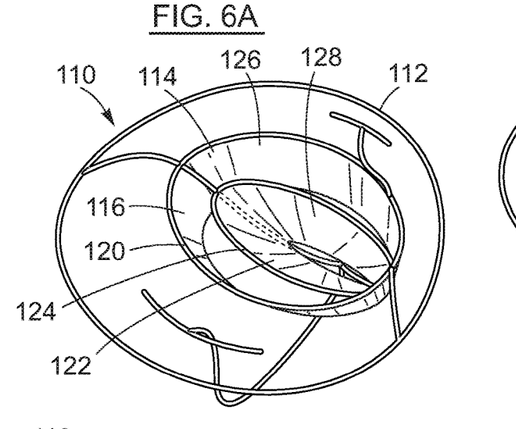
FIGS. 6A-6D depict perspective (anterior), perspective (posterior), side, and top views, respectively, of a repair device during diastole according to an embodiment of the invention.
Figure 6B:
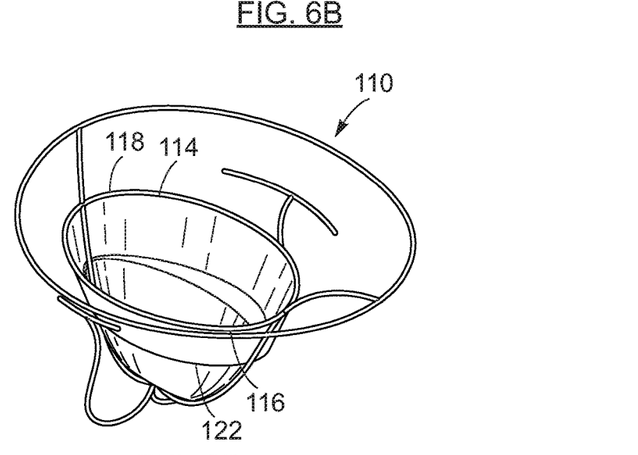
Figures 6C, 6D:
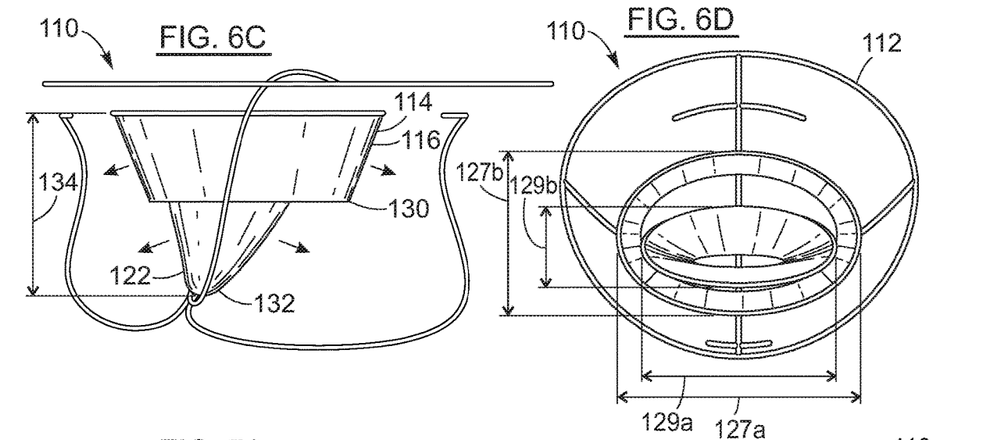

FIGS. 3A-3C depicts the anchor element 52 of a repair device 50, with the anchor element 52 including an upper anchor portion 56 configured to sit within the left atrium (e.g., just above/adjacent the native mitral valve annulus), a lower anchor portion 58 configured to extend into and anchor within the upper portion of the left ventricle (e.g., just below/adjacent the native mitral valve annulus), and a central portion 60 configured to support a sealing element. In the particular embodiment depicted, the upper anchor portion 56 comprises a continuous loop 62, which is secured to the central anchor portion 60 by connecting links 64. The lower anchor portion 58 comprises an anterior anchor arm 66*a* and a posterior anchor arm 66*p*. The anterior anchor arm 66*a* is configured to avoid interfering with the anterior leaflet, which is accomplished by having the anterior anchor arm 66*a* extend around the "swing" area through which the anterior leaflet moves, so that the anterior leaflet does not engage against the anterior anchor arm 66*a*. The anterior anchor arm 66*a* may include anterior distal fingers 68*a*, which extend away from the anterior anchor arm 66*a* and are configured to engage heart tissue underneath the native valve annulus. Similarly, the posterior anchor arm 66*p* is configured to avoid interfering with the natural movement of the posterior leaflet by extending from the anchor frame and around the "swing" area through which the posterior leaflet moves, so that the posterior leaflet does not engage against the posterior anchor arm 66*p*. The posterior anchor arm 66*p* may include posterior distal fingers 68*p*, which extend away from the posterior anchor arm 66*p* and are configured to engage heart tissue underneath the native valve annulus. With the device deployed in a native mitral valve as depicted in FIGS. 2A-2D, the continuous loop 62 is positioned just above the native valve annulus, the anchor fingers 68*a*, 68*p* are positioned just below the native valve annulus, the tissue at or adjacent the native valve annulus is compressed between the anchor fingers 68*a*, 68*p* and the continuous loop 62 to thereby secure the anchor 52 in place.

The anchor frame may be formed of various biocompatible materials, including metals and polymers. For example, memory materials such as Nitinol may be used, thereby forming an anchor frame that can be compressed onto/into a catheter for minimally-invasive/percutaneous delivery and then will expand to its "memorized" shape upon release from the catheter. Non-memory materials such as stainless steel or cobalt chromium are also within the scope of the invention. The anchor frame may include a biocompatible covering, such as of a dacron or other fabric. The biocompatible covering may encourage tissue ingrowth to promote tissue anchoring. The biocompatible covering may alternatively resist tissue ingrowth.

As depicted in FIGS. 3D-3G, a sealing element 54 is secured to the central anchor portion 60. The sealing element 54 forms a relatively smooth surface against which the native valve leaflets may engage during systole in order to assist in sealing the mitral valve in order to prevent valve regurgitation. The sealing element may preferably wrap around the exterior and/or interior of the central anchor portion 60, so that the wireform elements of the central anchor portion 60 are covered and/or encapsulated by the sealing element in order to prevent the native valve leaflets from contacting any frame elements of the central anchor portion 60. The sealing element 54 comprises an anterior side 70*a* and a posterior side 70*p*, each side configured to engage its respective mitral valve leaflet (i.e., anterior or posterior leaflet) during systole. The sealing element 54 further comprises a large proximal opening 72 and a smaller distal opening 74. The proximal opening 72 may be held permanently open by a portion of the central anchor portion 60, such as by the proximal continuous frame loop 76 depicted. The distal opening 74 may be a slit in the sealing element distal end, which can act in a similar fashion to a so-called duckbill valve where material on either side of the slit distal opening 74 engages inward in order to seal the distal opening 74 during systole but then are pressed outward in order to open the distal opening during diastole.

The sealing element proximal opening 72 is somewhat elliptical, having a major diameter 73*a* that may be between 25 and 45 mm and a minor diameter 73*b* that may be between 15 and 35 mm. Similarly, the sealing element distal opening 74 (when in the open configuration) is also somewhat elliptical, having a major diameter 75*a* that may be between 10 and 20 mm and a minor diameter 75*b* that may be between 2 and 8 mm. The sealing element 54 may have an overall height 55 of between 10 and 25 mm.

The connecting links 64 of the embodiment of FIGS. 3A-3G may be positioned around the perimeter of the device 50 such that, when the device 50 is deployed in a native mitral valve, one of the connecting links 64 is positioned adjacent each of the two (2) commissures of the native valve leaflets. Connecting links may be positioned around the perimeter such that one of the connecting links is circumferentially aligned with each of the anterior/posterior anchor arms 66*a*, 66*p*.

Sealing elements according to the invention may be formed of various biologically compatible materials, including metals, fabrics, plastics, and tissue. Some materials that may be used for such sealing elements include materials currently used in forming leaflets of prosthetic heart valves. For example, synthetic materials (e.g., polymers such as thermoplastic elastomers or resins, including polyurethane and silicone, etc.), natural/treated tissue (e.g., valve leaflet tissue, bovine or equine pericardium, etc.), fabrics (e.g., Dacron), etc. may be used.

Note that other configurations of the anchor frame are also within the scope of the invention. For example, the anterior and posterior anchor arms 66a, 66p may be complemented by, or replaced by, anchor arms that are positioned to extend from the device at other positions around the circumference (as seen from above as in FIG. 3E) of the device. For example, anchor arms may be positioned to extend from the device in a positon adjacent the links 64, such that the anchor arms will be positioned adjacent the valve commissures when the device is deployed in a native heart valve.

FIGS. 4A-4D depict a device 80 similar to that of FIGS. 3A-3G, having an anchor frame 82 and a sealing element 84. The main difference in the embodiment of FIGS. 4A-4D is that the anchor frame 82 comprises segmented upper frame portions 86 (as compared to the continuous loop upper frame portion 62 of FIGS. 3A-3E). The segmented upper frame portions 86 may be conducive to easy crimping of the device 80 onto/into a delivery catheter, and may provide for a smaller delivery diameter of the device 80 in the compressed configuration.

FIGS. 5A-5D depict a device 90 similar to that of FIGS. 3A-3G, having an anchor frame 92 and a sealing element 94. The main difference in the embodiment of FIGS. 5A-5D is that the anchor frame 92 comprises only two (2) connecting links 96 connecting the upper frame portion 98 to the central frame portion 100 (as opposed to the four (4) connecting links of the embodiment of FIGS. 3A-3E). The two (2) connecting links 96 of the embodiment of FIGS. 5A-5D may be positioned around the perimeter of the device such that, when the device 90 is deployed in a native mitral valve, the connecting links 96 are positioned adjacent the commissures of the native valve leaflets. The upper frame portion 98 depicted is the same shape and size as that depicted in FIGS. 3A-3E, and also defines a periphery similar in size and shape to that depicted in FIGS. 4A-4D (except for the non-continuous nature of the upper frame portion of FIGS. 4A-4D). The upper frame portion 98 is somewhat elliptical, having a major diameter 99a that may be between 40 and 70 mm and a minor diameter 99b that may be between 30 and 60 mm. The overall height 102 of the wireframe and the device 90 may be between 15 and 30 mm.

In a further embodiment of the invention depicted in FIGS. 6A-6D and 7A-7B, a device 110 comprises an anchor frame 112 similar to that depicted in FIGS. 5A-5D. The sealing element 114 has an upper sealing element portion 116 secured to an upper ring 118 of the central anchor portion 120, and a lower sealing element portion 122 secured to a lower ring 124 of the central anchor portion 120. The upper openings 126, 128 of the sealing element portions 116, 122 are secured to and held permanently open by the respective upper and lower rings 118, 124. The upper sealing element upper opening 126 and upper ring 118 are generally elliptical and may have a major diameter 127a that may be between 25 and 45 mm, and a minor diameter 127b that may be between 15 and 35 mm. The lower sealing element upper opening 128 and lower ring 124 are generally elliptical and may have a major diameter 129a that may be between 20 and 40 mm, and a minor diameter 129b that may be between 5 and 20 mm. The combination of the upper and lower sealing element portions 116, 122 have an overall height 134 of between 10 and 25 mm.

Figure 7A:
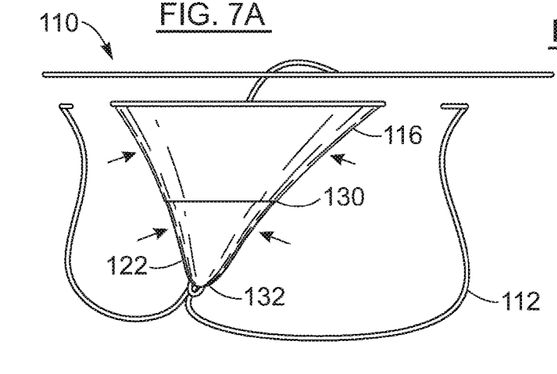
FIGS. 7A-7B depict side and top views, respectively, of the repair device of FIGS. 6A-6D during systole.
Figure 7B:
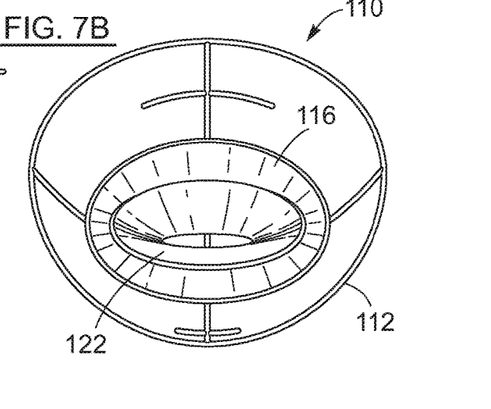
Figure 8A:
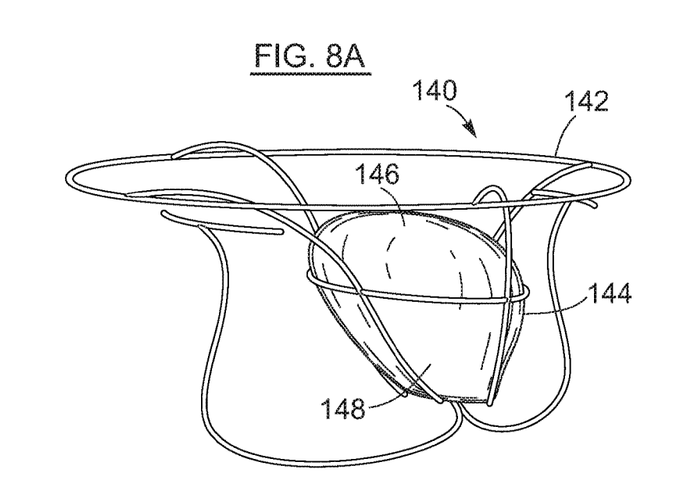
FIGS. 8A-8D depict perspective (anterior), perspective (posterior), side, and top views, respectively, of a repair device according to an embodiment of the invention.
Figure 8B:
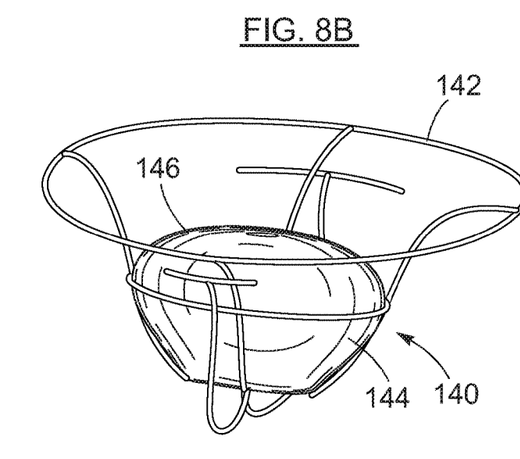
Figure 8C:
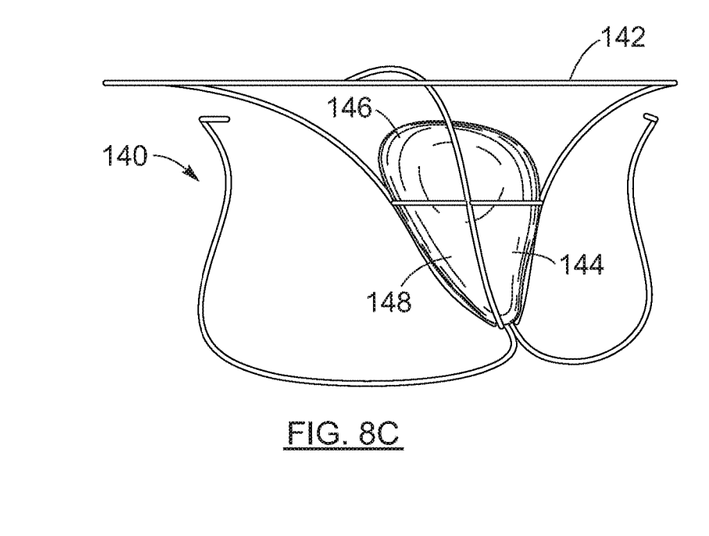
Figure 8D:
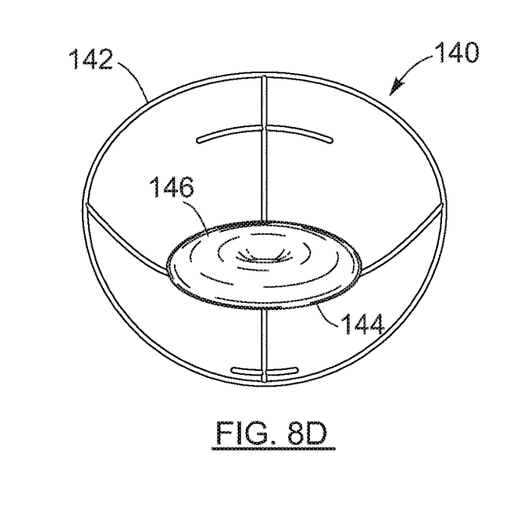

As depicted in FIGS. 6A-6D, during diastole the lower edges 130, 132 of the sealing element portions 116, 122 are pushed apart to open the sealing element and permit fluid flow therethrough. As depicted in FIGS. 7A-7B, during systole the lower edges 132 of the lower sealing element portion 122 are compressed together (like a so-called duckbill valve) in order to seal the lower end of the lower sealing element portion 122, while the lower edges 130 of the upper sealing element portion 116 engage against the upper part of the lower sealing element portion 122. The result is that during systole the sealing element 114 is closed to prevent fluid flow therethrough, while during diastole the sealing element 114 is at least partially open to permit fluid flow therethrough.

FIGS. 8A-8D depict a device 140 having a support anchor element 142 similar to that depicted in FIGS. 3A-3E, but the sealing element 144 defines a fully closed surface which is held in position and may also be radially supported in its expanded condition by the support anchor element 142. The sealing element 144 may have a shape that is optimized to minimize flow resistance during diastole while providing maximum coaptation with the native valve leaflets during systole. The sealing element 144 may have a shape that is custom made for a particular patient based on the physical properties of the native valve leaflets of the particular patient. For example, medical personnel may scan or otherwise examine a patient's native heart valve (including native leaflet function/coaptation/shape), and determine an optimized shape to maximize coaptation with the native mitral valve leaflets. The optimized shape may be determined and designed using computer-aided flow modeling and design techniques. A custom sealing element 144 may then be manufactured according to the custom design. The sealing element, whether custom or otherwise, may be formed using various methods, such as 3-D printing (e.g., as a solid or hollow construction, and using rigid and/or flexible materials). The sealing element 144 may be configured to be inflated (e.g., with a liquid), such as may be done during or just after deployment of the device. The sealing element may preferably have a rounded/streamlined, hydrodynamic upper surface 146 which promotes easy flow of blood downward over the upper surface diastole, and a streamlined hydrodynamic lower surface 148 that promotes easy passage/shedding of blood flow downward over and past the lower surface 148 during diastole while also providing a shape that is conducive to proper coaptation of the native valve leaflets against the lower surface 148 during systole.

Figure 9A:
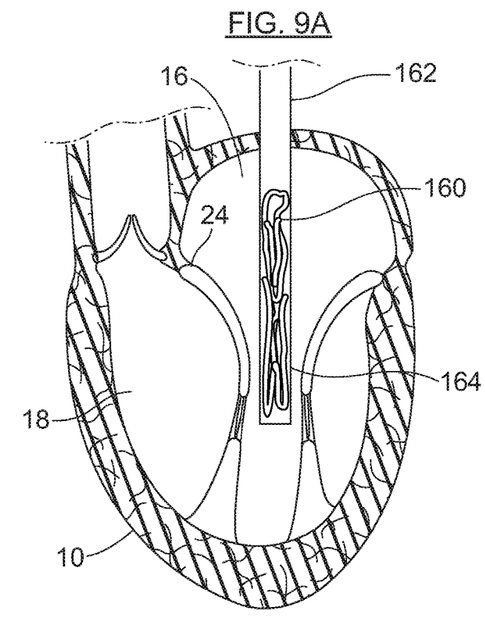
FIGS. 9A-9D depict a device being percutaneously deployed in a heart according to an embodiment of the invention.
Figure 9B:
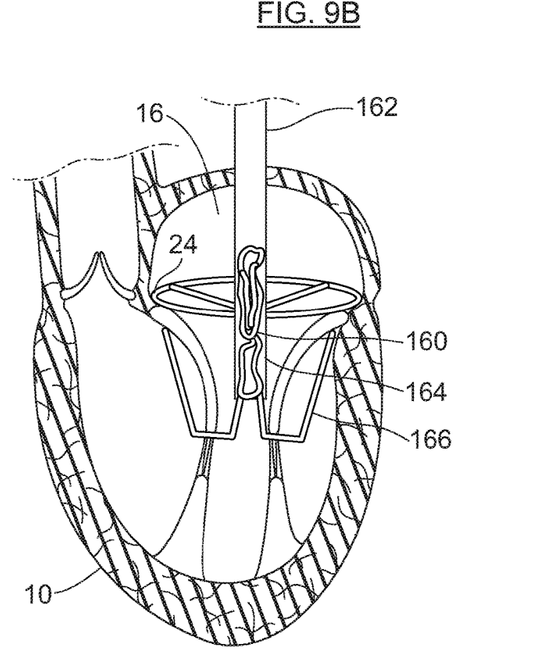
Figure 9C:
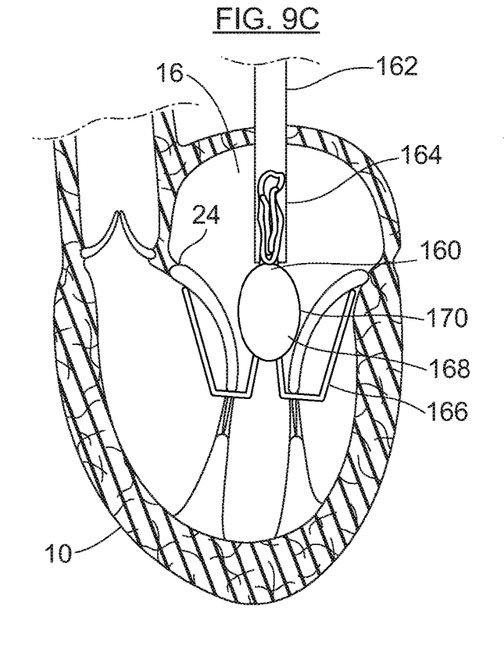
Figure 9D:
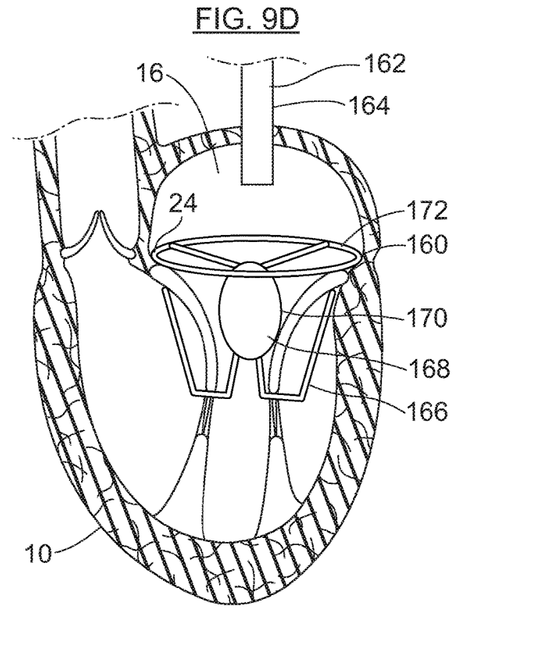

Devices according to the invention may be deployed as a part of various repair systems and methods. For example, in FIG. 9A a device 160 is secured within a distal end 164 of a delivery catheter 162, and the distal end 164 is advanced percutaneously or minimally-invasively into the mitral valve 24 of the patient via the left atrium 16 of a heart 10. In FIG. 9B the lower anchor portion 166 is expanded into contact with heart tissue below the mitral valve 24 as the device 160 begins to be released from the catheter 162. In FIG. 9C the sealing element 168 and central anchor portion 170 are expanded between the leaflets 42a, 42p of the mitral valve 24. In FIG. 9D, upper anchor portion 172 is expanded into contact with heart tissue above the mitral valve 24 as the device 160 is fully released from the catheter 162. With the position and function of the device 160 confirmed (such as via radioscopy and/or other methods of remote viewing), the catheter 162 is then withdrawn from the patient.

Figure 10A:
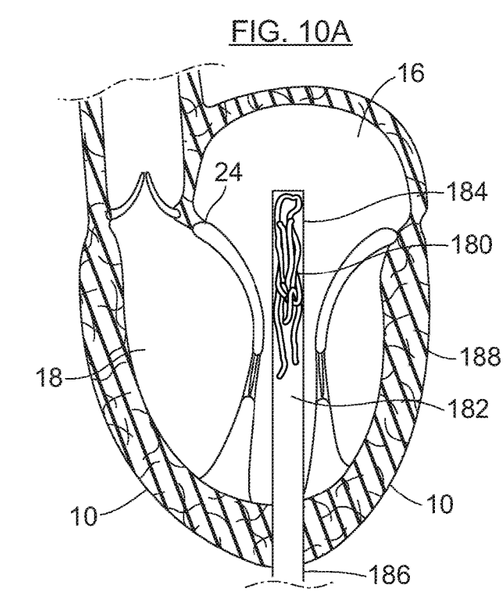
FIGS. 10A-10D depict a device being transapically deployed in a heart according to an embodiment of the invention.
Figure 10B:
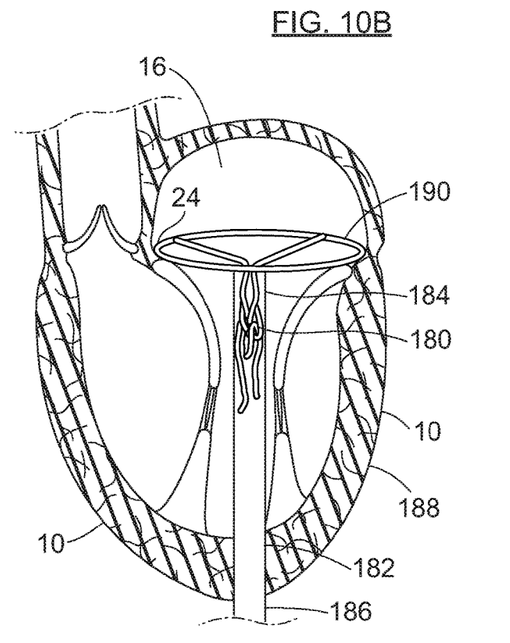
Figure 10C:
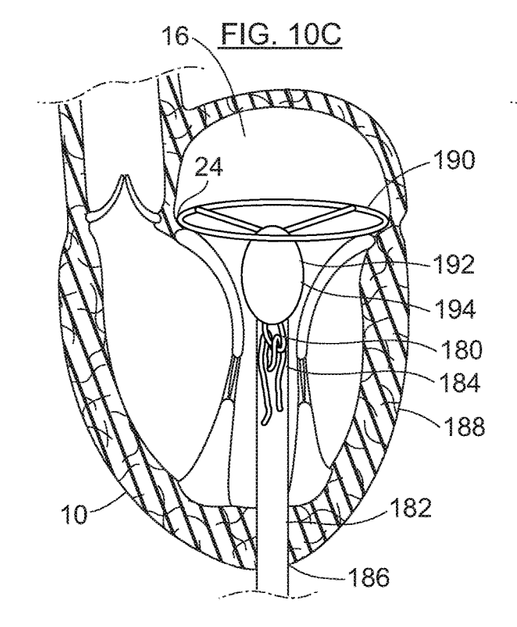
Figure 10D:
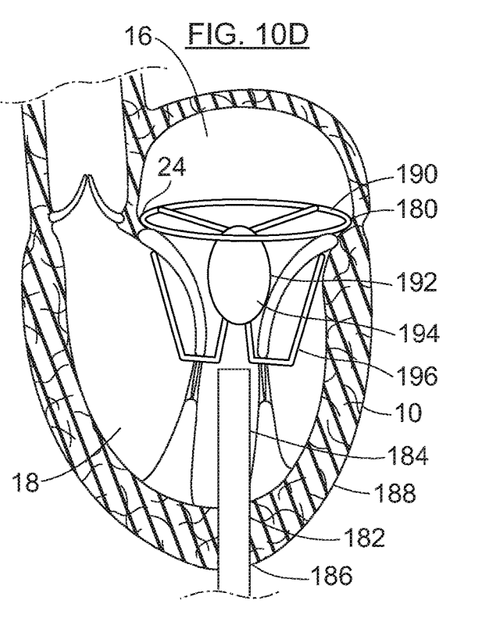

FIGS. 10A-10D depicts an additional system and method for deploying a device 180 in a heart 10 according to embodiments of the invention. In FIG. 10A, a device 180 is secured within a distal end 184 of a delivery catheter 182, and the catheter distal end 184 is advanced via an opening 186 in the heart wall 188 (e.g., via an opening in a wall of the left ventricle 18, such as a transapical opening) and into the mitral valve 24 of the patient. In FIG. 10B, the upper anchor portion 190 is expanded into contact with heart tissue above the mitral valve 24 (i.e., in the left atrium 16) as the device 180 begins to be released from the catheter 182. In FIG. 10C the sealing element 192 and central anchor portion 194 are expanded between the leaflets 42a, 42p of the mitral valve 24. In FIG. 10D, the lower anchor portion 196 is expanded into contact with heart tissue below the mitral valve 24 (i.e., in the upper portion of the left ventricle 18) as the device 180 is fully released from the catheter 182. With the position and function of the device 180 confirmed (such as via radioscopy and/or other methods of remote viewing), the catheter 182 is then withdrawn from the patient.

If the user (e.g., surgeon or other medical staff) is not satisfied with the initial positioning of all or part of the device, the device or parts thereof may be withdrawn (completely or partially) into the catheter and then re-deployed at the desired position. For example, if after initial deployment the sealing element is positioned too high or too low with respect to the mitral valve leaflets, the device or parts thereof can be at least partially withdrawn into the catheter and then re-deployed at a position higher or lower than the previous position.

Radiopaque markers or other visibility-enhancing markers may be included with the device in order to make the device and key elements thereof more clearly visible when the device is deployed or inspected using fluoroscopy or other visualization techniques. For example, enhanced visibility markers such as radiopaque markers may be secured to portions of the device such as connecting tabs (e.g., element 96 in FIGS. 5A-5D) 64 that are intended to align with the commissures of the native valve leaflets, or with other portions of the device such as the anterior/posterior arms and or fingers of the lower anchor portion (e.g., elements 66a, 66p, 68a, 68p), etc.

Note that FIGS. 3A-3F, 4A-4D, 5A-5D, 6A-6D, and 8A-8D are computer-generated to-scale drawings where dimensions are to scale within each drawing. All dimensions listed are by way of example, and devices according to the invention may have dimensions outside those specific values and ranges. Although in some of the drawings the sealing element material is depicted as extending between frame portions of central anchor elements but with the anchor elements uncovered, in various embodiments of the invention (including each of the embodiments of the invention depicted in the drawings) the sealing element material may preferably wrap around the exterior and/or interior of the central anchor portion, so that the wireform frame elements of the central anchor portion are covered and/or encapsulated by the sealing element in order to prevent the native valve leaflets from contacting any frame elements of the central anchor portion.

Although the specific embodiments discussed above are directed toward mitral valve repair, the invention may also be applicable for use in repairing other heart valves, including the aortic, tricuspid, and pulmonary valves.

Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise.

The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

What is claimed is:

1. A device for treating a mitral valve, comprising:
 a sealing element comprising:
  an upper ring;
  a lower ring;
  an upper sealing element secured to and held open by the upper ring, the upper sealing element defining a first upper opening and including upper anterior and posterior leaflet contact surfaces; and
  a lower sealing element secured to and held open by the lower ring, the lower sealing element defining a second upper opening and including lower anterior and posterior leaflet contact surfaces; and
 an anchoring element comprising:
  an at least partially elliptical atrial anchoring frame coupled to the upper ring of the sealing element; and
  one or more ventricular anchoring arms extending upward from a bottom of the sealing element, the one or more ventricular anchoring arms being disposed outside of the sealing element;
 wherein the first upper opening has an area that is greater than an area of the second upper opening.

2. The device of claim 1, wherein the sealing element and the anchoring element are collapsible and expandable.

3. The device of claim 1, wherein the one or more ventricular anchoring arms include one or more distal fingers that extend away from respective ones of the one or more ventricular anchoring arms.

4. The device of claim 1, further comprising a finger extending sideways away from at least one of the one or more ventricular anchoring arms.

5. The device of claim 1, wherein the one or more ventricular anchoring arms extend around a swing area for heart valve leaflets.

6. The device of claim 1, wherein the atrial anchoring frame comprises a continuous loop.

7. The device of claim 1, wherein the upper ring has a major diameter that is greater than a major diameter of the lower ring.

8. A medical implant device comprising:
an anchoring frame comprising:
an upper anchor structure;
a central anchor structure connected to the upper anchor structure by one or more connecting links extending from a perimeter of the upper anchor structure; and
a lower anchor structure comprising one or more anchor arms extending from a bottom portion of the anchoring frame; and
a sealing structure comprising:
an upper sealing element coupled to the anchoring frame, the upper sealing element defining a first upper opening and a first lower opening and including one or more upper outward-facing lateral contact surfaces; and
a lower sealing element that defines a second upper opening and a second lower opening and includes one or more lower outward-facing lateral contact surfaces;
wherein the upper sealing element and the lower sealing element are configured to provide a flow gap between the first lower opening of the upper sealing element and the second upper opening of the lower sealing element.

9. A medical implant device comprising:
an anchoring frame comprising:
an upper anchor structure; and
a central anchor structure connected to the upper anchor structure by one or more connecting links extending from a perimeter of the upper anchor structure;
an upper sealing element including:
one or more upper outward-facing lateral contact surfaces;
a first upper opening; and
a first lower opening; and
a lower sealing element including:
one or more lower outward-facing lateral contact surfaces;
a second upper opening; and
a second lower opening;
wherein:
the first upper opening is positioned above the second upper opening;
a lower end of the upper sealing element overlaps an upper end of the lower sealing element; and
the lower sealing element forms a duckbill valve.

10. The medical implant device of claim 8, wherein the upper anchor structure comprises a continuous loop structure.

11. The medical implant device of claim 8, wherein the upper anchor structure comprises circumferentially spaced circumferential loop segments.

12. The medical implant device of claim 8, wherein at least one of the upper sealing element or the lower sealing element is wrapped around at least one of an exterior or an interior of the central anchor structure.

13. The medical implant device of claim 12, wherein the central anchor structure comprises a ring structure connected to the one or more connecting links.

14. A medical implant device comprising:
an anchoring frame comprising:
an upper anchor structure; and
a central anchor structure connected to the upper anchor structure by one or more connecting links extending from a perimeter of the upper anchor structure;
an upper sealing element including:
one or more upper outward-facing lateral contact surfaces;
a first upper opening; and
a first lower opening; and
a lower sealing element including:
one or more lower outward-facing lateral contact surfaces;
a second upper opening; and
a second lower opening;
wherein:
the first upper opening is positioned above the second upper opening;
a lower end of the upper sealing element overlaps an upper end of the lower sealing element;
the first upper opening is larger than the first lower opening;
the first lower opening is larger than the second upper opening; and
the second upper opening is larger than the second lower opening.

15. The medical implant device of claim 14, wherein a major diameter of the first upper opening is greater than a major diameter of the second upper opening.

* * * * *